United States Patent [19]

Hall et al.

[11] Patent Number: 4,689,326
[45] Date of Patent: Aug. 25, 1987

[54] PROCESS FOR CONTROLLING HYPERLIPIDEMIA

[75] Inventors: Iris H. Hall, Chapel Hill; Steven D. Wyrick, Durham, both of N.C.; James M. Chapman, Jr., Columbia, S.C.

[73] Assignee: Research Corporation, New York, N.Y.

[21] Appl. No.: 788,200

[22] Filed: Oct. 17, 1985

[51] Int. Cl.[4] .............................................. A61K 31/55
[52] U.S. Cl. ..................................... 514/217; 514/824
[58] Field of Search .................... 514/217; 260/239 D

[56] References Cited

U.S. PATENT DOCUMENTS

| | | | |
|---|---|---|---|
| 2,619,484 | 11/1952 | Wenner | 260/239 D |
| 2,693,465 | 11/1954 | Schmidt et al. | 260/239 D |
| 3,017,337 | 1/1962 | Spiegelberg et al. | 260/239 D |
| 3,075,966 | 1/1963 | Hawthorne et al. | 260/239 D |
| 3,116,283 | 12/1963 | Boller et al. | 260/239 D |
| 3,551,414 | 12/1970 | Hawthorne et al. | 260/239.3 T |
| 3,668,232 | 6/1972 | Hawthorne et al. | 260/239.3 T |
| 3,821,201 | 6/1974 | Pessolano et al. | 260/239.3 T |

OTHER PUBLICATIONS

Journal of Pharmaceutical Sciences, vol. 73, No. 10, Oct. 1984, pp. 1482-1484; Chapman et al.

*Primary Examiner*—Leonard Schenkman
*Assistant Examiner*—Joseph A. Lipovsky
*Attorney, Agent, or Firm*—Scully, Scott, Murphy & Presser

[57] ABSTRACT

A process for controlling hyperlipidemia in mammals is disclosed. In this process a hyperlipidemia controlling effective amount of a compound having structural formula:

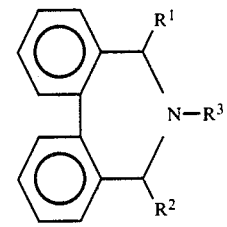

where $R^1$ is hydrogen, oxo, $C_1$-$C_6$ alkyl or $C_2$-$C_6$ alkanoyl; $R^2$ is hydrogen or oxo; and $R^3$ is hydrogen, $C_1$-$C_6$ alkyl, $C_2$-$C_6$ alkanoyl, $C_2$-$C_6$ carboxyalkyl, phenyl, benzyl or phenyl substituted with $C_1$-$C_6$ alkyl, $C_2$-$C_6$ alkanoyl, $C_1$-$C_6$ alkoxy or halo is applied to mammals. A pharmaceutical composition comprising the above class of compounds having the meanings given herein and a pharmaceutical carrier therefor is also taught.

9 Claims, No Drawings

PROCESS FOR CONTROLLING HYPERLIPIDEMIA

BACKGROUND OF THE DISCLOSURE

1. Field of the Invention

The present is directed to a process for controlling hyperlipidemia. More specifically, the present invention is directed to a process for controlling hyperlipidemia by treatment with a class of compounds comprising 3,4,5,6-dibenzohomopiperidine and substituted 3,4,5,6-dibenzohomopiperidines.

2. Backround of the Prior Art

Hyperlipidemia, a condition associated with elevated serum cholesterol, phospholipid and/or triglycerides blood levels, is the base cause of a whole class of illnesses which exact a terrible toll in death and infirmity as well as economic loss associated with lost productive activity and expensive medical treatment. It is only necessary to mention one of the most serious conditions known in man, athereosclerosis, probably the most serious of the hypolidemic induced diseases, to appreciate the importance of developing treatment regimes that are effective in controlling this condition.

Because of the importance of hyperlipidemia, many compounds have been proposed to lower serum cholesterol, phospholipid and triglyceride blood levels in mammals. For example, U.S. Pat. No. 4,499,303 discloses a novel class of N-benzoyl and N-benzoylsulfamates as well as benzoylsulfonamides useful in this application.

Another class of compound disclosed as useful in reducing serum cholesterol and triglycerides blood levels in mammals is U.S. Pat. No. 4,395,417. This patent describes the use of cyclic imides, diones, reduced diones and analogs thereof useful in this application.

The compound 3,4,5,6-dibenzohomopiperidine is known in the art. A process for its manufacture is provided in U.S. Pat. No. 2,693,465. This patent identifies the compound by another name, 6,7-dihydro-5H-dibenz(c,e)azepine. This patent refers to a still earlier patent, U.S. Pat. No. 2,619,484, which disclose a class of tricyclic amines which includes this compound recited to be useful as a therapeutic agent in the treatment of epinephrine.

An electrochemical process for the preparation of 3,4,5,6-dibenzohomopiperidine is the subject of U.S. Pat. No. 3,017,337. The patent indicates that this compound is useful as an intermediate in the manufacture of 6-allyl-6,7-dihydro-5H-dibenz(c,e)azepine. The latter compound is recited as having utility as a medicinal adrenergic blocking agent.

U.S. Pat. No. 3,075,966 sets forth still another method of making 3,4,5,6-dibenzohomopiperidine and related compounds which are again recited to be useful in inhibiting or reversing the physiological effect of epinephrine.

Yet still another process for making this class of compounds is disclosed in U.S. Pat. No. 3,116,283 which states that the 6-substituted 6,7-dihydro-5H-dibenz-(c,e)-azepin is useful as sympatholytic agent.

The compound 3,4,5,6-dibenzohomopiperidin-2-one is also known in the prior art. U.S. Pat. Nos. 3,551,414 and 3,668,232 both disclose this compound whose utility can be implied from the teachings of the patent. That is, hydrolysis of this compound yields the corresponding amino acid which is useful in producing azepines which can be used to inhibit or reverse the physiological effect of epinephrine.

U.S. Pat. No. 3,821,201 discloses a whole class of novel substituted 3,4,5,6-dibenzohomopiperidin-2-ones denoted in the patent as dibenzo(c,e)azepin-5-ones. The '201 patent recites that these compounds have potent anti-inflammatory, anti-pyretic and analgesic properties.

The above remarks establish the continuing need for newer and more effective compounds in the treatment of hyperlipidemic disorders.

SUMMARY OF THE INVENTION

It has now been discovered that a class of 3,4,5,6-dibenzohomopiperidine compounds, many of the species of which are new, exhibit greater hypolipidemic activity than do the compounds known in the prior art which are presently used to treat hyperlipidemic disorders.

In accordance with the instant invention, a process is provided for controlling hyperlipidemia in mammals by applying to mammals a hyperlipidemia controlling effective amount of a compound having the structural formula

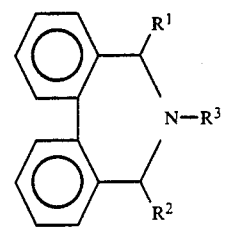

where $R^1$ is hydrogen, oxo, $C_1-C_6$ alkyl or $C_2-C_6$ alkanoyl; $R^2$ is hydrogen or oxo; and $R_3$ is hydrogen, $C_1-C_6$ alkyl, $C_2-C_6$ alkanoyl, $C_2-C_6$ carboxyalkyl, phenyl, benzyl or phenyl substituted with $C_1-C_6$ alkyl, $C_2-C_6$ alkanoyl, halo, or $C_1-C_6$ alkoxy.

DETAILED DESCRIPTION

The present invention is directed to a process for controlling hyperlipidemia in mammals. Thus, the instant invention is directed to a process for controlling a whole host of mammalian diseases associated with increased serum cholesterol, serum triglycerides and/or serum phospholipid blood level. These conditions oftentimes are associated with a number of heart related diseases, among which the most serious is atherosclerosis.

The process for controlling hyperlipidemia comprises treating a mammal subject to one or more of these conditions with a hypolipidemic controlling effective amount of a compound having the structural formula

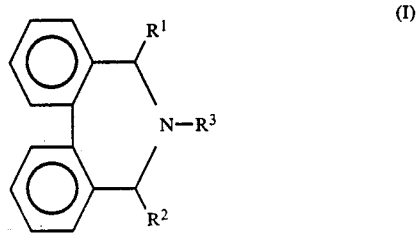

(I)

where $R^1$ is hydrogen, oxo, $C_1$–$C_6$ alkyl or $C_2$–$C_6$ alkanoyl; $R^2$ is hydrogen or oxo; and $R^3$ is hydrogen, $C_1$–$C_6$ alkyl, $C_2$–$C_6$ alkanoyl, $C_2$–$C_6$ carboxyalkyl, phenyl or phenyl substituted with $C_1$–$C_6$ alkyl, $C_2$–$C_6$ alkanoyl, halo or $C_1$–$C_6$ alkoxy.

More preferably, the present invention is directed to a process for controlling hyperlipidemia in which a hyperlipidemia controlling effective amount of the compound having the structural formula (I) wherein $R^1$ is hydrogen, oxo, $C_1$–$C_5$ alkyl or $C_2$–$C_4$ alkanoyl; $R^2$ is hydrogen or oxo; and $R^3$ is hydrogen, $C_2$–$C_4$ alkanoyl, $C_2$–$C_4$ carboxyalkyl, $C_1$–$C_5$ alkyl, phenyl, benzyl or phenyl substituted with $C_1$–$C_3$ alkyl, $C_1$–$C_3$ alkoxy, $C_2$–$C_4$ alkanoyl or chloro.

Of the compounds having the structural formula (I) those defined by $R^1$ and $R^2$ as being hydrogen or oxo in combination with $R^3$ having the meaning hydrogen are disclosed in the prior art. However, many of the other substituted compounds having this structural formula are new. Among these compounds are the 3,4,5,6-dibenzopiperidines substituted in the 2-position by $C_1$14 $C_6$ alkyl or $C_1$–$C_6$ alkanoyl. For example, many of compounds having the structural formula (I) where $R^1$ is $C_1$–$C_6$ alkyl or $C_1$–$C_6$ alkanoyl and $R^2$ and $R^3$ are hydrogen are novel. That class of compounds are formed by a procedure disclosed by Uffer and Schletter [*Hew. Chim. Acta.*, 31, 1397 (1948)] for the reduction of imides to amines. In this procedure lithium aluminum hydride is reacted with the appropriate N-alkyldiphenimide or N-alkanoyldiphenimide to produce the 2-alkyl or alkanoyl substituted 3,4,5,6-dibenzohomopiperidine.

Another class of new compounds useful in the process of the present invention are those which comprises a class of substituted diphenimides. The substituted diphenimides are those compounds having the structural formula (I) where $R^1$ and $R^2$ are both oxo and wherein $R^3$ is any of those substituents defined therefor except hydrogen.

In the case where $R^3$ is $C_1$14 $C_6$ alkyl these compounds are obtained by treating diphenimide with potassium carbonate and the appropriate alkyl halide in anhydrous dimethylformamide (DMF). In the case where the $R^3$ is $C_1$14 $C_6$ alkanoyl, this ketone is synthesized by the reaction of diphenimide with methyl vinyl ketone in the presence of sodium ethoxide. Where the $R^3$ substituent is $C_2$–$C_6$ carboxyalkyl, diphenic anhydride is reacted with beta-alanine. To produce substituted phenyldiphenimides an appropriately substituted aniline is reacted with diphenic anhydride to produce the intermediate diphenimic acid which is dehydrated to the desired substituted phenyldiphenimide by refluxing with acetic anhydride and a catalytic amount of sodium acetate. It is noted that phenyldiphenimide is known in the art as are certain substituted phenimides.

Among the preferred compounds having the structural formula (I), whose substituents, $R^1$, $R^2$ and $R^3$, are within the contemplation of the present invention are 3,4,5,6-dibenzohomopiperidine, 3,4,5,6-dibenzohomopiperidin-2-one, diphenimide, 2-methyl-3,4,5,6-dibenzohomo-piperidine, 2-ethyl-3,4,5,6-dibenzohomopiperidine, 2-propyl-3,4,5,6-dibenzohomopiperidine, 2-butyl-3,4,5,6-dibenzohomopiperidine, 2-pentyl-3,4,5,6-dibenzohomopiperidine, 2-(3-oxobutyl)-3,4,5,6-dibenzopiperidine, N-methyldiphenimide, N-ethyldiphenimide, N-propyldiphenimide, N-butyldiphenimide, N-pentyldiphenimide, N-benzyldiphenimide, N-(3-oxobutyl)diphenimide, N-(2-carboxyethyl)-diphenimide, N-phenyldiphenimide, N-(2-methoxythyl)-phenyldiphenimide, N-(3-methoxy)phenyldiphenimide, N-(4-methoxy)-phenyldiphenimide, N-(2-methyl)-phenyldiphenimide, N-(3-methyl)-phenyldiphenimide, N-(4-methyl)-phenyldiphenimide, N-(2-ethyl)phenyldiphenimide, N-(3-ethyl)-phenyldiphenimide, N-(4-ethyl)-phenyldiphenimide, N-(2-chloro)-phenyldiphenimide, N-(3-chloro)-phenyldiphenimide, N-(4-chloro)phenyldiphenimide, N-(2-acetyl)-phenyldiphenimide, N-(3-acetyl)-phenyldiphenimide and N-(4-acetyl)-diphenimide. It is emphasized that this listing is not inclusive and other compounds within the meaning of structural formula (I) defined by the meanings of $R^1$, $R^2$ and $R^3$ are within the contemplation of this invention.

The process of the present invention employs compounds having the structural formula (I) wherein $R^1$, $R^2$ and $R^3$, have the meanings given above, to control hyperlipidemia. This is accomplished, as stated above, by treating mammals subject to this general condition with a hyperlipidemia controlling effective amount of one of these the compounds. In a preferred embodiment of the process of the present invention, a hyperlipidemia controlling effective amount of the compound is provided by treatment with one of the compounds of the present invention provided in a concentration of between about 10-60 milligrams per kilogram of mammalian weight per day. More preferably, the compounds utilized in the process of the present invention are applied at a rate in a range of between about 12 and 40 milligrams per kilogram per day. Most preferably, the hyperlipidemia controlling effective amount of the compounds of the present invention is in the range of between 15 and 30 milligrams per kilogram of mammalian weight per day.

In another aspect of the present invention a pharmaceutical composition is provided. In this aspect of the invention a composition comprising a hyperlipidemia controlling effective amount of the compound having the structural formula (I) where $R^1$ is hydrogen, oxo, $C_1$14 $C_6$ alkyl or $C_2$–$C_6$ alkanoyl; $R^2$ is hydrogen or oxo; $R^3$ is hydrogen, $C_2$–$C_6$ carboxyalkyl, phenyl, benzyl or phenyl substituted with $C_1$–$C_6$ alkyl, $C_1$–$C_6$ alkoxy, $C_2$–$C_6$ alkanoyl or halo and a pharmaceutically acceptable carrier therefor is provided.

In a preferred embodiment, the composition of the present invention comprises a hyperlipidemia controlling effective amount of the compound having the structural formula (I) where $R^1$ is hydrogen, oxo, $C_1$–$C_5$ alkyl or $C_2$–$C_4$ alkanoyl; $R^2$ is hydrogen or oxo; and $R^3$ is hydrogen, $C_1$–$C_5$ alkyl, $C_2$–$C_4$ alkanoyl, $C_2$–$C_4$ carboxyalkyl, phenyl, benzyl or phenyl substituted with $C_1$–$C_3$ alkyl, $C_1$–$C_3$ alkoxy, $C_2$–$C_4$ alkanoyl or chloro and a pharmaceutically acceptable carrier therefor.

It is emphasized that in a particularly preferred embodiment of this invention the hyperlipidemia controlling effective aomounts of the compounds of the present invention are those concentration ranges recited above in the discussion of the process of the present invention.

The following examples are given to illustrate the scope of the present invention. Because these examples are given for illustrative purposes only, the invention embodied herein should not be limited thereto.

EXAMPLE 1

Preparation of 2-Alkyl-3,4,5,6-Dibenzohomopiperidines (Compounds No. 4-8)

A solution of N-alkyldiphenimide (0.03 mol) in a 150 ml of dry tetrahydrofuran (THF), wherein the alkyl of said N-alkyldiphenimide is the alkyl in the 2-alkyl-3,4,5,6-dibenzohomopiperidine final product, was added dropwise to a suspension a lithium aluminum hydride (0.10 mol) in 125 ml of ether. The mixture was stirred under reflux for 16 hours. The excess hydride was decomposed by the dropwise addition of a saturated solution of sodium sulfate. The resulting thick mass was filtered. The filtrate was extracted with 1.0 M hydrochloric acid. The aqueous extracts were combined. The combined extracts were, in turn, extracted with ether, made alkaline with sodium hydroxide and extracted again with ether. The organic extracts were dried utilizing sodium sulfate and evaporated under reduced pressure to produce a crude product. The crude product was purified by column chromatography wherein the eluant was ethyl acetate.

Each of the purified N-2-alkyl-3,4,5,6-dibenzohomopiperidines compounds so prepared were weighed and their yield determined. In addition, the purified compounds were analyzed.

The results of this example are summarized in Table 1.

EXAMPLE 2

Preparation of 2-(3-Oxobutyl)-3,4,5,6-Dibenzohomopiperidine (Compound No. 9)

A solution of N-(3-oxobutyl)-diphenimide (2.93 g; 0.01 mol) in 50 ml of dry THF was added dropwise to a suspension of lithium aluminum hydride (1.6 g; 0.04 mole) in 40 ml of anhydrous ether. The mixture was stirred under reflux for 16 hours and the crude product was formed in accordance with the procedure utilized in Example 1. The crude alcohol product was purified by column chromatography.

The purified alcohol was oxidized by adding it (200 mg; 8.0 mmol) to a suspension of pyridinium chlorochromate (500 mg; 0.02 mol) in 10 ml of dry methylene chloride. This mixture was stirred at room temperature for 2.5 hours. The solvent was then evaporated and the resultant tarry mass dissolved in a 10% sodium hydroxide solution, extracted with ether, dried with sodium sulfate and evaporated to obtain the crude product. This product was purified by column chromatography (9:1; ethyl acetate:methanol).

The purified product was obtained in a yield of a 100 mg (4%).

The analysis of this product was as follows:

$^1$H-NMR (CDCl$_3$): lambda, 7.45 (m, 8, aromatic), 3.36 (s, 4x, 2x—C$\underline{H}_2$), 2.80 (s, 4, —NC$\underline{H}_2$, —C$\underline{H}_2$CO) and 2.19 ppm (s, 3, —COC$\underline{H}_3$).

Analysis: Calculated for C$_8$H$_{19}$NO: C, 81.50; H, 7.16; N, 5.28. Found: C, 81.59; H, 7.28; N, 5.40.

EXAMPLE 3

Preparation of N-Alkyldiphenimides (Compound Nos. 11-15)

Potassium carbonate (0.072 mole) was added to a solution of diphenimide (0.18 mole) in anhydrous dimethylformamide (100 ml). This mixture was stirred and the appropriate alkyl halide (0.02 mole) was added thereto. These reactants were left at room temperature for 3-4 hours. At the end of this time, water (300 ml) was added and a precipitate formed. The precipitate was filtered and dried. Recrystallization of the product from a suitable solvent afforded the appropriate product.

TABLE 1

| Comp'd No. | Alkyl of 3,4,5,6-dibenzohomopiperidine | Yield, % | $^1$HNMR (CDCl$_3$) | Analysis |
|---|---|---|---|---|
| 4 | methyl | 21 | δ, 7.44 (m, 8, aromatic) 3.34 (s, 4, 2x-C$\underline{H}_2$), 2.43 ppm (s, 3, —C$\underline{H}_3$) | Calc for C$_{15}$H$_{15}$N: C, 86.12; H, 7.18; N, 6.70. Found: C, 86.17; H, 7.21; N, 6.56 |
| 5 | ethyl | 24 | δ, 7.40 (m, 8, aromatic) 3.38 (s, 4, 2x-C$\underline{H}_2$), 2.62 (q, 2, —NC$\underline{H}_2$), & 1.20 ppm (t, 3, —C$\underline{H}_3$) | Calc for C$_{16}$H$_{17}$N: C, 86.10; H, 7.62; N, 6.28. Found: C, 85.86; H, 7.90; N, 6.26. |
| 6 | propyl | 18 | δ, 7.44 (m, 8, aromatic) 3.32 (s, 4, 2x-C$\underline{H}_2$), 2.49 (t, 2, —NC$\underline{H}_2$), 1.37–1.88 (m, 2, —C$\underline{H}_2$), & 0.92 ppm (t, 3, —C$\underline{H}_3$) | Calc for C$_{17}$H$_{19}$N: C, 86.07; H, 8.02; N, 5.91. Found:C, 85.91; H, 7.04; N, 5.94. |
| 7 | butyl | 28 | δ, 7.42 (m, 8, aromatic) 3.39 (s, 4, 2x-C$\underline{H}_2$), 2.6 (t, 2, —NC$\underline{H}_2$), 1.32–1.75 (m, 4, 2x-C$\underline{H}_2$), & 0.92 ppm (t, 3, —C$\underline{H}_3$) | Calc for C$_{18}$,H$_{21}$,N: C, 86.05; H, 8.26; N, 5.57. Found: C, 86.28; H, 8.49; N, 5.53. |
| 8 | pentyl | 16 | δ, 7.45 (m, 8, aromatic) 3.42 (s, 4, 2x-C$\underline{H}_2$) 2.58 (t, 2, —NC$\underline{H}_2$), 1.25–1.72 (m, 6, 3x-C$\underline{H}_2$), & 0.95 ppm (t, 3, —C$\underline{H}_3$) | Calc for C$_{19}$H$_{23}$N: C, 86.04; H, 8.67; N, 5.28. Found: C, 85.92; H, 8.72; N, 5.14 |

Table 2 below summarizes the alkyl substituted N-diphenimides made in accordance with Example 3. Table 2 includes the identity of the recrystallization solvent, the yield, the melting point and the identifying NMR data.

Analysis: Calculated for $C_{17}H_{13}NO_4$: C, 69.15; H, 4.44; N, 4.74. Found: C, 68.95; H, 4.50; N, 4.69.

$^1$HNMR ($\delta$,TMS): 7.50–7.88 (m, 8H, aromatic)
4.15 (p, 2H, —NC$\underline{H}_2$),
2.58 (c, 2H, —HC$\underline{H}_2$CO)

TABLE 2

| Comp'd No. | Alkyl Subst. N—Diphenimide | Recrystallization Solv't | Yield, % | mp, °C | $^1$HNMR ($\delta$, TMS) |
|---|---|---|---|---|---|
| 11 | ethyl | hexane | 80 | 99–101 | 7.45–7.95 (M, 8H, aromatic) |
|  |  |  |  |  | 4.15 (q, 2H, —NC$\underline{H}_2$) |
|  |  |  |  |  | 1.30 (t, 3H, —C$\underline{H}_3$) |
| 12 | propyl | hexane | 84 | 91–93 | 7.50–7.80 (M, 8H, aromatic) |
|  |  |  |  |  | 4.12 (t, 2H, —NCH$_2$C$\underline{H}_2$) |
|  |  |  |  |  | 1.62–1.95 (m, 2H, —NCH$_2$C$\underline{H}_2$) |
|  |  |  |  |  | 1.00 (t, 3H, —C$\underline{H}_2$) |
| 13 | butyl | methanol | 78 | 59–60 | 7.30–7.75 (m, 8H, aromatic) |
|  |  |  |  |  | 4.04 (t, 2H, —NC$\underline{H}_2$) |
| 14 | pentyl | acetone | 67 | 69–71 | 7.45–7.90 (m, 8H, aromatic) |
|  |  |  |  |  | 4.25 (t, 2H, —NC$\underline{H}_2$) |
|  |  |  |  |  | 0.50–1.85 (m, 9H, 2x-C$\underline{H}_2$ + CH$_3$) |
| 15 | benzyl | benzene | 85 | 127–129 | 7.30–7.85 (m, 8H, aromatic) |
|  |  |  |  |  | 5.35 (s, 2H, —NC$\underline{H}_2$) |

EXAMPLE 4

Preparation of N-(3-Oxobutyl)-Diphenimide (Compound No. 16)

Twenty-two grams of diphenimide (0.1 mol) was suspended in ethyl acetate (150 ml) to which a catalytic amount of sodium ethoxide was added. The mixture was stirred and heated to 70° C. Methyl vinyl ketone (13.6 g, 0.16 mol) was added dropwise to the mixture over a 10 minute period. This mixture was stirred under reflux for two hours. At the end of this time glacial acetic acid was added until the solution was neutralized. The solvent was removed in vacuo and the residue recrystallized from methanol to produce the ketone product.

This product, N-(3-oxobutyl)-diphenimide, was analyzed as follows: Calculated for $C_{18}H_{15}NO_3$: C, 73.71; H, 5.15; N, 4.78. Found: C, 74.00; H, 5.13, N, 4.76.

EXAMPLE 5

Preparation of N-(2-Carboxyethyl)-Diphenimide (Compound No. 17)

A mixture of diphenic anhydride (7.0 g, 0.03 mol), beta- alanine (2.7 g, 0.03 mol) and DMF(60 ml) was stirred under reflux for six hours. The solvent was removed in vacuo, and the resulting residue dissolved in a acetic anhydride (50 ml) and glacial acetic acid (10 ml). The solution was stirred under reflux for two hours after which the volatile material was removed in vacuo. The residue was recrystallized from isopropanol to produce the acid product, N-(2-carboxyethyl)-diphenimide.

The product was found to have a melting point of 169°–171° C. It was obtained in a yield of 17%.

EXAMPLE 6

Preparation of N-(Substituted Phenyl)-Diphenimide Compound Nos. 19–21, 23, 25–29 and 31–33

N-(substituted phenyl)-diphenimides were each prepared in the same manner. In each case an equivalent amount of the appropriate amine was added to a solution of diphenic anhydride (3.0 g, 0.013 mol) in chloroform (40 ml). The mixture was stirred and refluxed gently for two hours. The solvent was removed in vacuo and the residue was treated with acetic anhydride (20 ml) and sodium acetate (1.0 g). The resulting mixture was heated to reflux for 30 minutes. The mixture was then triturated with hot water to remove excess acetic anhydride. The product was filtered, washed with water, dried and recyrstallized in a suitable solvent.

The products obtained, including their yield, are summarized in Tables 3 and 4. Table 3 provides the identity of the compound, its melting point, the recrystallization solvent and the yield. Table 4 provides analytical data identifying the compounds.

TABLE 3

| Comp No. | N—Substituted Phenyl Diphenimide | mp, °C. | Recrystallization Solvent | Yield % |
|---|---|---|---|---|
| 19 | 2-methoxyphenyl | 185–187 | Benzene | 73 |
| 20 | 3-methoxyphenyl | 162–165 | Benzene | 66 |
| 21 | 4-methoxyphenyl | 133–136 | Benzene | 80 |
| 23 | 3-methylphenyl | 149–151 | Acetone | 90 |
| 25 | 2-ethylphenyl | 120–122 | Benzene | 53 |
| 26 | 3-ethylphenyl | 89–92 | Benzene | 66 |
| 27 | 4-ethylphenyl | 142–144 | Acetone | 60 |
| 28 | 2-cholorphenyl | 212–218 | Benzene | 75 |
| 29 | 3-chlorophenyl | 155–157 | Acetone | 84 |
| 31 | 2-acetylphenyl | 149–142 | Chloroform | 63 |
| 32 | 3-acetylphenyl | 167–169 | Chloroform | 81 |
| 33 | 4-acetylphenyl | 196–198 | Chloroform | 70 |

TABLE 4

| Comp No | $^1$HNMR ($\delta$, TMS) | Formula | % Calc | | | % Found | | |
|---|---|---|---|---|---|---|---|---|
|  |  |  | C | H | N | C | H | N |
| 19 | 7.05–7.90 (m, 12H, | $C_{21}H_{15}NO_3$ | 76.59 | 4.56 | 4.25 | 76.48 | 4.71 | 4.27 |

TABLE 4-continued

| Comp No | $^1$HNMR ($\delta$, TMS) | Formula | % Calc C | H | N | % Found C | H | N |
|---|---|---|---|---|---|---|---|---|
| | aromatic) 3.80 (s, 3H, —O$\underline{CH_3}$) | | | | | | | |
| 20 | 7.28–8.00 (m, 9H, aromatic) 6.85–7.10 (m, 3H, aromatic) 3.85 (s, 3H, —O$\underline{CH_3}$) | $C_{21}H_{15}NO_3$ | 76.59 | 4.56 | 4.25 | 76.59 | 4.69 | 4.31 |
| 21 | 7.35–7.85 (m, 8H, aromatic) 6.95 (d, 4H, aromatic) 3.82 (s, 3H, —O$\underline{CH_3}$) | $CH_{21}H_{15}NO_3$ | 76.59 | 4.56 | 4.25 | 76.66 | 4.47 | 4.17 |
| 23 | 7.05–8.14 (m, 12H, aromatic) 2.41 (s, 3H, —$\underline{CH_3}$) | $CH_{21}H_{15}NO_2$ | 80.51 | 4.79 | 4.47 | 80.64 | 4.91 | 4.50 |
| 25 | 7.14–8.18 (m, 12H, aromatic) 2.45 (q, 2H, —$\underline{CH_2}$) 1.17 (t, 3H, —$\underline{CH_3}$) | $C_{22}H_{17}NO_2$ | 80.73 | 5.17 | 4.28 | 80.66 | 5.50 | 4.18 |
| 26 | 6.99–8.15 (m, 12H, aromatic) 2.65 (q, 2H, —$\underline{CH_2}$) 1.26 (t, 3H, —$\underline{CH_3}$) | $C_{22}H_{17}NO_2$ | 80.73 | 5.17 | 4.28 | 80.63 | 5.37 | 4.23 |
| 27 | 7.07–7.96 (m, 12H, aromatic) 2.72 (q, 2H, —$\underline{CH_2}$) 1.26 (t, 3H, —$\underline{CH_3}$) | $C_{22}H_{17}NO_2$ | 80.73 | 5.17 | 4.28 | 80.53 | 5.36 | 4.25 |
| 28 | Not Determined | $C_{20}H_{12}NO_2Cl$ | 71.75 | 3.89 | 4.78 | 71.68 | 3.82 | 4.20 |
| 29 | Not Determined | $C_{20}H_{12}NO_2Cl$ | 71.75 | 8.89 | 4.78 | 71.50 | 3.73 | 4.56 |
| 31 | 7.44–8.26 (m, 12H, aromatic) 2.61 (s, 3H, —CO$\underline{CH_3}$) | $C_{20}H_{15}NOH_3$ | 77.42 | 4.40 | 4.11 | 77.15 | 4.57 | 4.01 |
| 32 | 7.25–8.05 (m, 12H, aromatic) 2.55 (s, 3H, —CO$\underline{CH_3}$) | $C_{20}H_{15}NO_3$ | 77.42 | 4.40 | 4.11 | 77.44 | 4.64 | 4.12 |
| 33 | 7.28–8.28 (m, 12H, aromatic) 2.64 (s, 3H, —CO$\underline{CH_3}$) | $C_{20}H_{15}NO_3$ | 77.42 | 4.40 | 4.11 | 77.29 | 4.45 | 4.24 |

EXAMPLE 7

Testing of Normal Mice

Suspensions of Compounds Nos. 1–9 were prepared wherein the compounds were suspended in an aqueous 1% carboxymethylcelluose solution, homogenized and administered to $CF_1$ male mice, each weighing approximately 25 grams, intraperitoneally on a daily basis for 16 days. The dosage was, with the exception of one compound, 20 milligrams of the active compound per kilogram of mouse weight per day. On days 9 and 16 blood was obtained by tail vein bleeding. The blood serum was separated by centrifugation for three minutes. Serum cholesterol levels were determined by a modification of the Liebermann-Burchard reaction. Serum was also collected on day 16 and the triglycerides content was determined by a commercial kit, BioDynamics/bnc Single Vile Colorimetric Method 348201. Each compound was tested on a group of six mice.

In addition to the above-described treated mice, untreated control groups of six mice were similarly tested on days 9 and 14 or 16 to determine their serum cholesterol and triglycerides blood levels. Table 5 reports the percent control, based on the serum cholesterol and serum triglyceride levels of the treated mice compared to the untreated controls. Table 5 also includes the standard deviation indicating the level of confidence of these numbers.

COMPARATIVE EXAMPLE 1

Testing with 1% Carboxymethylcellulose (Compound No. C1)

The testing regime of Example 7 was repeated. However, the mice of this comparative example were treated intraperitonally with only the suspending agent, an aqueous solution of 1% carboxymethylcellulose (CMC). The results of this test are also summarized in Table 5.

COMPARATIVE EXAMPLE 2

Testing with Clofibrate (Compound No. C2)

Example 7 was repeated substituting clofibrate, a compound used in the prior art to lower serum cholesterol and serum triglyceride levels. The clofibrate was administered as a suspension in an aqueous 1% solution of carboxymethylcellulose. However, unlike the compounds of the present invention which were administered at a dosage of 20 mg/kg day, ip, this compound was administered at the elevated concentration of 150 mg/kg day, ip. The results of this test is also presented in Table 5.

TABLE 5

| Compd No | Compd Name | Daily Dosage mg/kg, ip | Serum Cholesterol Control, % Day 9 | Serum Cholesterol Control, % Day 16 | Serum Triglicerides Control, % Day 16 |
|---|---|---|---|---|---|
| 1 | Diphenimide | 20 | 81 ± 7* | 82 ± 4 | 81 ± 7 |
| 2 | 3,4,5,6-Dibenzo-homopiperidin-2-one | 20 | 84 ± 6 | 49 ± 4 | 73 ± 5 |
| 3 | 3,4,5,6-Dibenzo-homopiperidine | 10 | 61 ± 5 | 50 ± 5 | 48 ± 5 |
|   |   | 20 | 68 ± 4 | 48 ± 4 | 49 ± 5 |
|   |   | 40 | 67 ± 6 | 54 ± 4 | 44 ± 6 |
|   |   | 60 | 69 ± 5 | 51 ± 4 | 55 ± 6 |
| 4 | 2-Methyl-3,4,5,6 dibenzohomopiperidine | 20 | 75 ± 6 | 61 ± 5 | 66 ± 6 |
| 5 | 2-Ethyl-3,4,5,6 dibenzohomopiperidine | 20 | 67 ± 5 | 59 ± 4 | 60 ± 4 |
| 6 | 2-Propyl-3,4,5,6 dibenzohomopiperidine | 20 | 78 ± 6 | 65 ± 5 | 73 ± 6 |
| 7 | 2-Butyl-3,4,5,6 dibenzohomopiperidine | 20 | 82 ± 7 | 59 ± 6 | 52 ± 7 |
| 8 | 2-Pentyl-3,4,5,6 dibenzohomopiperidine | 20 | 71 ± 6 | 67 ± 5 | 71 ± 4 |
| 9 | 2-(3-Oxobutyl)-3,4,5,6, dibenzo-homopiperidine | 20 | 69 ± 8 | 56 ± 7 | 45 ± 5 |
| C1 | 1% Soln of CMC | — | 100 ± 5$^a$ | 100 ± 6$^b$ | 100 ± 6$^c$ |
| C2 | Clofibrate | 150 | 88 ± 7 | 87 ± 5 | 75 ± 5 |

Footnotes:
*± standard deviation
$^a$118 mg/dl
$^b$122 mg/dl
$^c$137 mg/dl

EXAMPLE 8 and COMPARATIVE EXAMPLE 3

Testing of Normal Rats

In Example 8 a set of six Sprague Dawley male rats, each weighing approximately 350 grams, were orally treated with a concentration of 20 mg per kilogram of rat weight per day, again suspended in a 1% aqueous solution of CMC. The dosage was applied orally by an intubation needle. On days 9 and 16 serum cholesterol and serum triglycerides blood levels of the rats were measured utilizing th procedure of Example 7. Test results of this test appear in Table 6.

In comparative Example 3 a similar group of six Sprague Dawley male rats were similarly treated and tested. However, these rats were administered only the suspending agent, the 1% aqueous solution of CMC. The results of this test is included on Table 6.

A control group of six similar Sprague Dawley male rats were untreated but tested on Days 9 and 16 in accordance with the tests administered to the treated rats. Table 6 reports the percent control based on the decrease in serum cholesterol and serum triglycerides of the treated rats compared to the levels measured in the untreated control group.

TABLE 6

| Comp'd | Dosage | % Control ± Standard Deviation Serum Cholesterol Day 9 | Serum Cholesterol Day 16 | Serum Triglycerides Day 9 | Serum Triglycerides Day 16 |
|---|---|---|---|---|---|
| 3,4,5,6-dibenzo-homopiperidine | 20 | 75 ± 5 | 64 ± 3 | 54 | 54 |
| 1% CMC | — | 100 ± 8$^a$ | 100 ± 7$^b$ | 100 ± 6$^c$ | 100 ± 7$^d$ |

Notes:
$^a$73 mg/dl
$^b$78 mg/dl
$^c$110 mg/dl
$^d$112 mg/dl

EXAMPLE 9

Enzymatic Studies Involving the Use Of 3,4,5,6-Dibenzohomopiperidine

In vitro enzymatic studies were undertaken using 10% homogenates of $CF_1$ male mouse liver with 50-200 M of compound 3,4,5,6-dibenzohomopiperidine. In addition, in vivo enzymatic studies were performed, again using 10% liver homogenates (prepared in 0.25 M sucrose plus 0.001 M (ethylenedinitrilo)-tetraacetic acid, ph 7.25 from $CF_1$ male mice obtained after administering 3,4,5,6-dibenzohomopiperidine for 16 days at a concentration ranging from 10 to 60 mg/kg/day, intraperitoneally.

The following enzyme activities were determined by following standard literature procedures: acetyl coenzyme synthetase; adenosine triphosphate dependent citrate lyase; mitochondrial citrate exchange; cholesterol/7 hydroxylase; 3-hydroxy-3-methyl-glutaryl coenzyme A reductase; acetyl coenzyme A carboxylase activity; fatty acid synthetase activity; sn-glycerol-3-phosphate acyl transferase activity; phosphatidate phosphohydrolase activity; cholesterol acyl transferase; and heparin activated hepatic lypoprotein lipase. Protein was determined for all enzyme assays by the Lowry et al. technique (J. Biol. Chem, 193, 265 (1951)).

The results of these studies are tabulated in Table 7. Specifically, Table 7A provides data generated in vitro and Table 7B summarizes the in vivo results.

TABLE 7A

| In Vitro Enzyme Activity (N = 6) | Percent Control, % ± SD | | | |
|---|---|---|---|---|
| | Control | 50 μM | 100 μM | 200 μM |
| Mitochondrial Citrate Exchange | 100 ± 8[a] | 99 ± 6 | 97 ± 5 | 99 ± 7 |
| ATP Dependent Citrate Lyase | 100 ± 6[b] | 87 ± 5 | 38 ± 3 | 33 ± 4 |
| Acetyl CoA Synthetase | 100 ± 5[c] | 112 ± 6 | 100 ± 7 | 101 ± 6 |
| HMG CoA Reductase | 100 ± 8[d] | 95 ± 5 | 151 ± 9 | 255 ± 8 |
| Cholesterol-7 Hydroxylase | 100 ± 4[e] | 68 ± 7 | 72 ± 5 | 98 ± 7 |
| Acyl CoA Cholesterol Acyl | 100 ± 6[f] | 60 ± 6 | 59 ± 5 | 3 ± 1 |
| Acetyl CoA Carboxylase | 100 ± 6[g] | 84 ± 6 | 100 ± 7 | 99 ± 5 |
| Fatty Acid Synthetase | 100 ± 8[h] | 91 ± 7 | 92 ± 8 | 101 ± 9 |
| sn-Glycerol-3-Phosphate Acyl Transferase | 100 ± 7[i] | 35 ± 6 | 34 ± 5 | 51 ± 4 |
| Phosphatidate Phosphohyrolase | 100 ± 6[j] | 45 ± 4 | 44 ± 8 | 50 ± 6 |
| Hepatic Lipoprotein Lipase | 100 ± 5[k] | 90 ± 7 | 89 ± 6 | 72 ± 5 |

FOOTNOTES
[a] 30.8% exchange of mitochrondrial citrate;
[b] 30.5 mg citrate hydrolyzed/gm wet tissue/20 min.;
[c] 28.5 mg acetyl CoA formed/gm wet tissue/20 min.;
[d] 384,900 dpm cholesterol formed/gm wet tissue/60 min.;
[e] 224,000 dpm/ug microsomal protein;
[f] 4,808 dpm/mg microsomal protein/20 min.;
[g] 32,010 dpm/gm wet tissue/30 min.;
[h] 37,656 dpm/gm wet tissue/20 min.;
[i] 537,800 dpm/gm wet tissue/20 min.;
[j] 16.7 uP$_i$/gm wet tissue/15 min.;
[k] 278,583 dpm/gm wet tissue/hr.

TABLE 7B

| In Vivo Enzyme Activity (N = 6) | Percent Control, % ± SD | | | | |
|---|---|---|---|---|---|
| | Control | 10 mg/kg | 20 mg/kg | 40 mg/kg | 60 mg/kg |
| ATP Dependent Citrate Lyase | 100 ± 7 | 73 ± 6 | 63 ± 4 | 62 ± 3 | 65 ± 5 |
| Acetyl CoA Synthetase | 100 ± 6 | 64 ± 6 | 95 ± 6 | 103 ± 8 | 81 ± 6 |
| HMG CoA Reductase | 100 ± 8 | 123 ± 5 | 133 ± 9 | 146 ± 7 | 124 ± 6 |
| Acetyl CoA Carboxylase | 100 ± 6 | 54 ± 6 | 57 ± 7 | 47 ± 5 | 60 ± 4 |
| Fatty Acid Synthetase | 100 ± 8 | 100 ± 8 | 114 ± 6 | 106 ± 7 | 110 ± 8 |
| sn-Glycerol-3-Phosphate Acyl Transferase | 100 ± 6 | 45 ± 7 | 68 ± 8 | 62 ± 6 | 81 ± 6 |
| Phosphatidate Phosphohydrolase | 100 ± 7 | 51 ± 4 | 47 ± 9 | 81 ± 6 | 100 ± 6 |

EXAMPLE 10

Lipid Extraction Studies in Mice

The CF$_1$ male mice that had been administered compound 3,4,5,6-dibenzohomopiperidine at four dosage levels as well as the control mice, were sacrificed and the liver, small intestine and fecal materials (24 hour collection) were removed, extracted and analyzed for cholesterol level, triglycerides level, neutral lipid content and phospholipid content. The results of these tests are summarized in Table 8. Table 8 reports the decrease in measured levels of these concentrations as a percentage of the level in the control. The control, it is noted, is always 100%.

TABLE 8

| | Concentration as a Function of Control, % (±SD) | | | | |
|---|---|---|---|---|---|
| | Control | 10 g/kg | 20 mg/kg | 40 mg/kg | 60 mg/kg |
| Lipid wt | 100 ± 6 | 92 ± 7 | 62 ± 6 | 112 ± 9 | 106 ± 8 |
| Cholesterol | 100 ± 7[a] | 83 ± 6 | 55 ± 5 | 114 ± 8 | 99 ± 5 |
| Neutral lipid | 100 ± 6[b] | 75 ± 6 | 50 ± 5 | 95 ± 6 | 90 ± 6 |
| Triglyceride | 100 ± 5[c] | 48 ± 4 | 37 ± 4 | 70 ± 5 | 74 ± 6 |
| Phospholipid | 100 ± 7[d] | 78 ± 6 | 100 ± 7 | 84 ± 7 | 91 ± 8 |
| Protein | 100 ± 6[e] | 98 ± 9 | 95 ± 8 | 103 ± 7 | 104 ± 8 |

FOOTNOTES
[a] 12.24 mg cholesterol/gm tissue
[b] 4.77 mg triglyceride/gm tissue
[c] 28.35 mg neutral lipid/gm tissue
[d] 4.39 mg phosphalipid (P)/gm tissue
[e] 4.5 mg protein/gm tissue

EXAMPLE 11

Lipid Extraction Studies in Rats

A group of six Sprague Dawley male rats were treated with 20 mg/kg/day of 3,4,5,6-dibenzohomopiperidine. The treatment was applied orally. An equal number of Sprague Dawley male rats, having approximately the same weight, were utilized as an untreated control. At the end of fourteen days the control and treated rats were sacrificed. Blood was collected from the abdominal aorta and lipoprotein fractions were obtained by the method of Hatch and Lees [*Adv. Lipid Rees.*, 6, 1 (1968)] and Havel et al. [*J. Clin Invest.*, 34, 1345 (1955)]. Each of the fractions were analyzed for cholesterol, triglycerides, neutral lipids, phospholipids and protein levels.

Table 9 summarizes the results of these analysis.

TABLE 9

| | | Concentration as a Function of Control, % ± SD | | | | |
|---|---|---|---|---|---|---|
| | Mg Lipid Wt | Cholesterol | Triglycerides | Neutral Lipids | Phospholipids | Protein |
| Liver | | | | | | |
| Control | 100 ± 7 | 100 ± 7[a] | 100 ± 6[b] | 100 ± 6[c] | 100 ± 8[d] | 100 ± 6[e] |
| Treated | 89 ± 7 | 65 ± 5 | 76 ± 6 | 80 ± 5 | 98 ± 9 | 97 ± 7 |
| Small Intestine | | | | | | |
| Control | 100 ± 6 | 100 ± 7[f] | 100 ± 5[g] | 100 ± 5[h] | 100 ± 7[i] | 100 ± 7[j] |
| Treated | 143 ± 5 | 130 ± 6 | 130 ± 6 | 149 ± 6 | 119 ± 6 | 118 ± 7 |
| Feces | | | | | | |
| Control | 100 ± 7 | 100 ± 6[k] | 100 ± 6[l] | 100 ± 8[m] | 100 ± 7[n] | 100 ± 5[o] |
| Treated | 102 ± 8 | 103 ± 7 | 99 ± 7 | 108 ± 9 | 108 ± 10 | 133 ± 8 |
| Chylomicrons | | | | | | |
| Control | — | 100 ± 7[p] | 100 ± 7[q] | 100 ± 8[r] | 100 ± 7[s] | 100 ± 6[t] |
| Treated | — | 77 ± 6 | 69 ± 6 | 69 ± 7 | 65 ± 5 | 106 ± 6 |
| VLDL | | | | | | |
| Control | — | 100 ± 6[u] | 100 ± 6[v] | 100 ± 7[w] | 100 ± 8[x] | 100 ± 7[y] |
| Treated | — | 40 ± 4 | 69 ± 5 | 63 ± 6 | 95 ± 7 | 96 ± 8 |
| LDL | | | | | | |
| Control | — | 110 ± 6[z] | 100 ± 7[aa] | 100 ± 6[bb] | 100 ± 8[cc] | 100 ± 8[dd] |
| Treated | — | .82 ± 8 | 73 ± 6 | 107 ± 9 | 94 ± 10 | 108 ± 9 |
| HDL | | | | | | |
| Control | — | 100 ± 7[ee] | 100 ± 6[ff] | 100 ± 7[gg] | 100 ± 6[hh] | 100 ± 6[ii] |
| Treated | — | 106 ± 5 | 40 ± 2 | 59 ± 5 | 64 ± 3 | 106 ± 7 |

FOOTNOTES
[a] 24.03 mg cholesterol/gm tissue
[b] 6.37 mg triglycerides/gm tissue
[c] 44.11 mg neutral lipid/gm tissue
[d] 7.19 mg phosholipid (P)/gm tissue
[e] 4.5 mg protein/gm wet tissue
[f] 7.82 mg/gm
[g] 1.12 mg/gm
[h] 6.98 mg/gm
[i] 2.06 mg/gm
[j] 42 mg/g
[k] 28.47 mg/gm
[l] 1.86 mg/gm
[m] 33.94 mg/gm
[n] 1.239 kg/gm
[o] 6.99 mg/gm
[p] 337 μg/ml
[q] 420 μg/ml
[r] 67 μg/ml
[s] 149 μg/ml
[t] 184 μg/ml
[u] 190 μg/ml
[v] 22 μg/ml
[w] 98 μg/ml
[x] 26 μg/ml
[y] 50 μg/ml
[z] 210 μg/ml
[aa] 45 μg/ml
[bb] 10 μg/ml
[cc] 41 μg/ml
[dd] 122 μg/ml
[ee] 544 μg/ml
[ff] 27 μg/ml
[gg] 620 μg/ml
[hh] 153 μg/ml
[ii] 657 μg/ml

EXAMPLE 12

Effect of 3,4,5,6-Dibenzohomopiperidine on $^3$H Cholesterol Distribution in Rats A group of 6 Sprague Dawley rats, each weighing approximately 300 g, were treated with 3,4,5,6-dibenzohomopiperdine applied orally at a dosage of 20 mg/kg per day for 4 days. Six similar Sprague Dawley rats were untreated and served as a control. On the 13th day, 10 μCi of $^3$H-cholesterol was administered orally. The rats were sacrificed and tissue samples were combusted or plated on filter paper, dried and digested for 24 hours in hyamine hydroxide at 40° C. and counted. Results of this test are reported as disintegrations per minute (DPM) per total organ. The results of this test are summarized in Table 10.

In Table 10, the average organ weight and feces of the treated and untreated rats are reported. The table indicates the concentration of $^3$H-cholesterol in the organs and feces of the treated and untreated (control) rats.

TABLE 10

| Tissue | Quantity, g Control | Quantity, g Treated | Control DPM | Control % Recov. | Treated DPM | Treated % Recovery |
|---|---|---|---|---|---|---|
| Brain | 1.97 | 1.93 | 16,430 | 0.303 | 9,216 | 0.162 |
| Heart | 1.26 | 1.20 | 25,517 | 0.471 | 25,692 | 0.452 |
| Lung | 1.82 | 1.77 | 148,046 | 2.732 | 124,180 | 2.183 |
| Liver | 14.16 | 13.93 | 1,569,396 | 28.964 | 1,343,450 | 23.615 |
| Spleen | 0.18 | 1.17 | 134,741 | 2.487 | 102,723 | 1.806 |
| Kidney | 2.64 | 2.60 | 65,020 | 1.200 | 37,096 | 0.652 |
| Stomach | 2.55 | 2.40 | 87,747 | 1.619 | 124,552 | 2.189 |
| Small Intestine | 10.17 | 10.34 | 2,033,713 | 37.533 | 2,191,623 | 38.525 |
| Large Intestine | 4.01 | 3.75 | 167,241 | 3.087 | 213,777 | 3.757 |
| Chyme | 8.57 | 9.82 | 425,615 | 7.855 | 667,840 | 11.739 |
| Feces | 4.88 | 6.90 | 713,502 | 13.168 | 822,719 | 14.462 |
| Adrenal | 0.712 | 0.712 | — | — | — | — |
| Plasma | — | — | 31,383 | — | 26,018 | — |

EXAMPLE 13

Hypolipidemic Activity of Compounds 1 and 10–33

Compounds 1 and 10-33, identified below in Table 11, were suspended by homogenation in a 1% aqueous solution of carboxymethylcellulose (CMC) such that a 0.2 ml dosage supplied a concentration of 20 mg/kg of the active compounds. The suspending agent, the 1% aqueous solution of CMC, was utilized as a control, applied in the same quantity, 0.2 ml. $CF_1$ male mice, maintained in groups of six, were fed Wayne Blox [trademark] laboratory animal show ad libitum with water. The mice, which each weighed approximately 25 g, were administered the drugs interperitoneally at approximately the same time. On days 9 and 16 approximately 1 ml of blood was taken from each of the animals by tail bleeding. After centrifugation to obtain serum, 25 microliter samples were assayed for total cholesterol utilizing the method of Ness et al. Serum triglyicerides were assayed, using a commercially available BioDynamics/bmc triglyiceride kit, on blood collected on the 16th day. By comparison to standards the milligram percent of cholesterol and milligram per deciliter concentration of triglicerides were calculated. Treated values were expressed as a percent of the level of the control animals plus or minus the standard deviation. The "T" values were obtained using the Student's "t" test.

The results of this test are summarized in Table 11.

TABLE 11

| Comp'd No. | N—R-Diphenimide where R is: | Concentration as a Function of Control, % ($\pm$SD) Serum Cholesterol 9 Day | Serum Cholesterol 16 Day | Serum Triglyceride 16 Day |
|---|---|---|---|---|
| Control | 1% CMC | 100 ± 5[a] | 100 ± 6[b] | 100 ± 6[c] |
| 1 | hydrogen | 81 ± 7 | 82 ± 4 | 81 ± 7* |
| 10 | methyl | 64 ± 7* | 63 ± 5* | 67 ± 6* |
| 11 | ethyl | 64 ± 6* | 62 ± 5* | 66 ± 7* |
| 12 | propyl | 69 ± 7* | 66 ± 6* | 57 ± 5* |
| 13 | butyl | 78 ± 7* | 77 ± 10 | 52 ± 5* |
| 14 | pentyl | 90 ± 8 | 69 ± 4 | 60 ± 5 |
| 15 | benzyl | 91 ± 7 | 61 ± 6* | 77 ± 7* |
| 16 | 3-oxobutyl | 77 ± 5* | 77 ± 7* | 90 ± 4 |
| 17 | 2-carboxyethyl | 88 ± 11 | 84 ± 6 | 75 ± 10* |
| 18 | phenyl | 97 ± 8 | 67 ± 6* | 62 ± 6* |
| 19 | 2-methoxyphenyl | 80 ± 8* | 67 ± 5* | 68 ± 5* |
| 20 | 3-methoxyphenyl | 84 ± 7 | 74 ± 7* | 72 ± 8 |
| 21 | 4-methoxyphenyl | 91 ± 7 | 84 ± 8 | 74 ± 6* |
| 22 | 2-methylphenyl | 78 ± 7* | 61 ± 6* | 65 ± 6* |
| 23 | 3-methylphenyl | 78 ± 7* | 76 ± 7* | 63 ± 6* |
| 24 | 4-methylphenyl | 57 ± 7* | 52 ± 6* | 60 ± 7* |
| 25 | 2-ethylphenyl | 82 ± 8 | 73 ± 6* | 84 ± 7 |
| 26 | 3-ethylphenyl | 95 ± 7 | 77 ± 7* | 66 ± 6* |
| 27 | 4-ethylphenyl | 101 ± 8 | 71 ± 5* | 70 ± 7* |
| 28 | 2-chlorophenyl | 67 ± 6* | 64 ± 5* | 65 ± 6* |
| 29 | 3-chlorophenyl | 81 ± 8 | 78 ± 8* | 87 ± 7 |
| 30 | 4-chlorophenyl | 74 ± 6* | 67 ± 5* | 64 ± 4* |
| 31 | 2-acetylphenyl | 79 ± 7* | 76 ± 6* | 58 ± 6* |
| 32 | 3-acetylphenyl | 77 ± 8* | 68 ± 6* | 58 ± 4* |
| 33 | 4-acetylphenyl | 80 ± 5* | 73 ± 5* | 70 ± 5* |

FOOTNOTES:
*p = 0.01
[a] = 118 mg %
[b] = 112 mg %
[c] = 137 mg/dl

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for controlling hyperlipidemia in mammals comprising applying to a mammal in need thereof a hyperlipidemia controlling effective amount of a compound having the structural formula

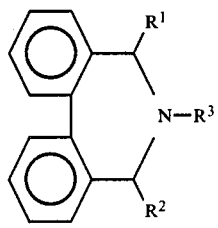

where $R^1$ is hydrogen, oxo, $C_1$–$C_6$ alkyl or $C_2$–$C_6$ alkanoyl; $R^2$ is hydrogen or oxo; $R^3$ is hydrogen, $C_1$–$C_6$ alkyl, $C_2$–$C_6$ alkanoyl, $C_2$–$C_6$ carboxylalkyl, phenyl, benzyl or phenyl substituted with $C_1$–$C_6$ alkyl, $C_1$–$C_6$ alkoxy, $C_2$–$C_6$ alkanoyl or halo.

2. A process with claim 1 wherein $R^1$ is hydrogen, oxo, $C_1$–$C_5$ alkyl, or $C_2$–$C_4$ alkanoyl; and $R^3$ is hydrogen, $C_2$–$C_4$ alkanoyl, $C_2$–$C_4$ carboxyalkyl, $C_1$–$C_5$ alkyl, phenyl, benzyl or phenyl substituted with $C_1$–$C_3$ alkyl, $C_1$–$C_3$ alkoxy, $C_2$–$C_4$ alkanoyl or chloro.

3. A process in accordance with claims 2 wherein said compound is 3,4,5,6-dibenzohomopiperidine.

4. A process in accordance with claim 2 wherein said compound is 3,4,5,6-dibenzohomopiperidin-2-one.

5. A process in accordance with claim 2 wherein $R^1$ and $R^2$ are both oxo.

6. A process in accordance with claim 2 wherein $R^1$ is $C_1$–$C_5$ alkyl or $C_2$–$C_4$ alkanoyl and $R^2$ and $R^3$ are both hydrogen.

7. A process in accordance with claim 1 wherein said compound is applied at a dosage of about 10 to 60 milligrams per kilogram of mammal weight per day.

8. A process in accordance with claim 7 wherein said compound is applied at a dosage of about 12 to 40 milligrams per kilogram of mammal weight per day.

9. A process in accordance with claim 8 wherein said compound is applied at a dosage in the range of between about 15 and 30 milligrams per kilogram of mammal weight per day.

* * * * *

UNITED STATES PATENT AND TRADEMARK OFFICE
CERTIFICATE OF CORRECTION

PATENT NO. : 4,689,326

DATED : August 25, 1987

INVENTOR(S) : Iris H. Hall et al.

Page 1 of 2

It is certified that error appears in the above-identified patent and that said Letters Patent is hereby corrected as shown below:

Column 1, line 7, add after "present" --invention--.

Column 3, lines 22, 40, 44 and Column 4, line 44, replace "$C_1 14C_6$" with --$C_1$-$C_6$--.

Column 4 line 61, replace "aomounts" with --amounts--.

Column 8, line 43, replace "recystallized" with --recrystallized--.

Column 8, Table 3, replace "149-142" with --142-149--.

Column 10, line 52, replace "intraperitonally" with --intraperitoneally--.

Column 11, line 43, replace "th" with --the--.

Column 11, line 49, replace "is" with --are--.

Column 12, line 50, replace "ph" with --pH--.

Column 13, Table 7A, replace "Phosphatidate Phosphohyrolase" with --Phosphatidate Phosphohydrolase--.

Column 14, Table 8, Footnote d, replace "phosphalipid" with --phospholipid--.

Column 14, line 68, replace "analysis" with --analyses--.

Column 17, line 60, replace "show" with --chow--.

Column 17, line 67, replace "triglyicerides" with --triglycerides--.

Column 18, line 18, replace "triglyiceride" with --triglyceride--.

UNITED STATES PATENT AND TRADEMARK OFFICE
CERTIFICATE OF CORRECTION

PATENT NO. : 4,689,326

DATED : August 25, 1987

INVENTOR(S) : Iris H. Hall et al.

It is certified that error appears in the above-identified patent and that said Letters Patent is hereby corrected as shown below:

Column 18, line 21, replace "triglicerides with triglycerides--.
Column 20, line 3 (Claim 3), replace "claims" with --claim--.

Signed and Sealed this

Twenty-sixth Day of April, 1988

Attest:

DONALD J. QUIGG

*Attesting Officer*  *Commissioner of Patents and Trademarks*